United States Patent [19]

Rosenbladt et al.

[11] Patent Number: 4,523,853
[45] Date of Patent: Jun. 18, 1985

[54] MEDICAL TEST REACTION AREA REFLECTED LIGHT PHOTOMETRIC DEVICE

[75] Inventors: Rudolf V. Rosenbladt, Bad Homburg; Klaus Nenninger, Mannheim; Rudolf Schüssler, Lampertheim, all of Fed. Rep. of Germany

[73] Assignee: Boehringer Mannheim GmbH, Mannheim, Fed. Rep. of Germany

[21] Appl. No.: 413,292

[22] Filed: Aug. 31, 1982

[30] Foreign Application Priority Data

Sep. 30, 1981 [DE] Fed. Rep. of Germany ....... 3138878

[51] Int. Cl.$^3$ ............................ G01N 21/47; G01J 1/06
[52] U.S. Cl. .................................. 356/446; 250/228; 250/237 R; 356/448
[58] Field of Search ............... 356/445, 446, 447, 448, 356/236; 250/228, 237 R, 227

[56] References Cited

U.S. PATENT DOCUMENTS

| | | |
|---|---|---|
| 2,358,020 | 9/1944 | Miller ............................ 250/227 X |
| 2,688,099 | 8/1954 | Bickley ....................... 250/237 R X |
| 3,327,583 | 6/1967 | Vanderschmidt et al. ..... 356/446 X |

FOREIGN PATENT DOCUMENTS 2466783 4/1981 France .

OTHER PUBLICATIONS

Arbeitsprinzip des Seralyzer ® pp. 6 & 7.
Blitzer et al., "Apparatus for Measuring the Reflectance of a Sample", *Research Disclosure* (Oct. 1978), pp. 61–62.

Primary Examiner—Vincent P. McGraw
Attorney, Agent, or Firm—Sprung, Horn, Kramer & Woods

[57] ABSTRACT

A device for reflected-light photometry, that determines the reflectivity of a specimen area which is part of an objective area specifically dedicated for the determination of certain properties, especially those of the reaction area of a medical-laboratory test strip. The device has a light source for illuminating the specimen area, preferably with diffuse light, and a photodetector that picks up light reflected from the specimen area. There is, in accordance with the invention, an opaque diaphragm with a particular shape, position, and mounting in the path of light between the specimen area and the detector.

16 Claims, 3 Drawing Figures

MEDICAL TEST REACTION AREA REFLECTED LIGHT PHOTOMETRIC DEVICE

BACKGROUND OF THE INVENTION

The present invention relates to a device for reflected-light photometry that determines the reflectivity of a specimen area, which is part of an objective area specifically dedicated for the determination of certain properties, especially those of the reaction area of a medical-laboratory test strip, with a light source for illuminating the specimen area, preferably with diffuse light, and a photodetector that picks up light reflected from the specimen area.

The utilization of test strips to detect medically significant components of body fluids (blood and urine) is increasing in importance. The body-fluid components that are studied result in reactions that occur on the test strips, that reveal themselves through changes in color, and that can be interpreted visually to arrive at a qualitative evaluation. The utilization of test strips and associated instruments to determine medically significant quantitative parameters is also becoming constantly more common. Very high demands with respect to precision are being made not only on the test strips but also on the instruments. The objective of the present invention is to increase the precision of the instruments.

Reflected-light photometry measures total reflectivity, which is made up of a diffuse component and an ordinary component. To determine both components together the reaction area is either illuminated directly and the diffuse reflection measured or diffusely and the direct reflection measured. The present invention relates specifically to the second type of process, and an Ulbricht globe is preferably utilized to illuminate the reaction area of a test strip with diffused light.

It is essential that the light picked up by the detector in reflected-light photometers of this design be reflected almost exclusively in practical terms from the part of the objective area that provides the properties to be detected and that will be called the specimen area herein and not be reflected from other objects that it may encounter or derive from extraneous sources. This requirement, which seems to be simple to fulfill, actually provides considerable problems when maximal precision is necessary, as in the photometry of test strips.

The instruments are subject to certain constraints that limit their performance. They must be as small and convenient as possible. Since they are often powered by batteries, the light reflected from the specimen area is often not very intense, and it is essential that it arrive as unobstructed as possible at the detector, with every possible source of interference being eliminated as completely as possible.

Since these instruments are manufactured on an industrial scale for use by laymen, especially diabetics monitoring their own sugar levels, it is also important that they be as inexpensive and simple to operate as possible, without loss of precision. Extremely narrow tolerances and time-consuming equilibration must also be avoided.

SUMMARY OF THE INVENTION

The object of the invention is to provide a more precise reflected-light photometer that is as simple as possible and in which in particular interference from marginal light not reflected from the specimen area will be suppressed so that the light that is reflected from it will arrive at the detector as unobstructed as possible, ensuring maximal performance subject to all operating conditions.

The invention attains this objective in a device of the type initially described but with an opaque diaphragm with a diaphragm surface that is shaped essentially like a hollow truncated cone, that has a light-absorbing inside area facing the axis of symmetry of the path of light between the specimen area and the detector, that is positioned in that path in such a way as to essentially symmetrically surround the axis of symmetry along part of its length, and that tapers up toward the detector, with the cross-section of its upper edge smaller than that of its lower edge.

The diaphragm, because it extends over a certain length of the path of the light and because its cross-section decreases essentially constantly from the specimen area towards the detector, will almost completely eliminate interference from marginal light without significantly diminishing the intensity of the light reflected from the specimen area into the detector. Only the light derived from the margin of the specimen area will be attenuated, to great advantage and in accordance with an evaluation curve that will be explained below.

The outstanding effectiveness of the type of diaphragm employed in the invention is demonstrated by a reflectivity of almost precisely zero being read off without supplementary correction when a completely absorbent specimen area is scanned. Practical tests indicate that the residual reflection resulting from scattered light will be less than 0.05% when the diaphragm employed in the invention is used, whereas a diaphragm of known design will leave 0.5%. The zero-point problems that are so familiar in the field will be solved with surprising economy of design.

The design of the diaphragm employed in the invention can be varied in several ways. Although the cross-section of the diaphragm along a plane perpendicular to the axis of symmetry of the path of light is preferably circular, it can also have a different shape, an ellipse or oval for example, when the specimen area being scanned is not circular.

The inside area of the diaphragm, which faces the path of the light, is light-absorbent, preferably black. It will preferably have a defined roughness of about 10 $\mu$m. It is especially practical and preferred when the component that contains the diaphragm consists completely of an appropriately selected black plastic.

It is also possible for the diaphragm to have a profile of discontinuous steps parallel to the axis of the path of light.

The only prerequisite for the invention is that the hole through the diaphragm widen from the detector toward the specimen area so that the marginal light that enters it and strikes its inside area will be reflected at such an angle that any components that are not absorbed will be thrown back against the surface and extinguished.

It is especially preferable for the top and bottom edges of the diaphragm and the border of the specimen area that is to have its reflectivity determined to be positioned approximately along a sheaf of straight lines that intersect and surround the axis of symmetry of the path of the light at a point inside the aperture through the diaphragm, between, that is, the planes defined by the top and bottom edges of the diaphragm, and that symmetrically surround the axis. This arrangement will result in an especially advantageous evaluation of the specimen area because the border zones of the reaction area, which are as a rule less homogeneous, will be screened out and the rays from the center of the area will make a greater contribution.

It is preferable to provide another diaphragm that surrounds the specimen area like a mask and has a light-absorbing surface that is essentially flat or concave toward the detector. This additional provision will further attenuate the especially critical marginal light that strikes the first diaphragm at a flat angle. The aperture through the second diaphragm will not, for practical reasons, exactly coincide with the border of the specimen area, but its edge will have a radius about 10% larger than the radius of the specimen area. Since the components of the systems will have to be manufactured to a certain tolerance, this will prevent part of the inner surface of the second diaphragm from intruding into the specimen area and contaminating the results.

In an especially desirable application of the invention, in which the specimen area is, as mentioned above, diffusely illuminated through an Ulbricht globe, a second photodetector for determining a known reference property of a surface of known reflectivity is preferred. It is also preferable for the inside surface of the Ulbricht globe to be the reference area, in which case both photodetectors in preferred embodiments of the invention will have diaphragms that are exactly alike in design and position. If the detectors, diaphragms, and specimen areas are thus positioned symmetrically to the light source and/or inside the globe, precision will be high. External influences like temperature variations and phenomena related to the age of the detectors will thus be compensated for, and both detectors will detect properties subject to the same conditions. Obviously the long-term operation of the device will be very efficient.

Using part of the inside surface of the Ulbricht globe as a reference area eliminates the need for a special separate standard. The device in accordance with the invention is especially effective over the long term because other areas of the inside surface of the globe will change over time, if they change at all, in exactly the same way as the reference area. The intensity with which the specimen area is illuminated will therefore change at the same rate as the reflectivity of the reference area, and both effects will be eliminated by the quotient construction that occurs as part of the evaluation.

In one preferred embodiment, the diaphragm and detector are positioned in the same mount, which is housed on radial arms in the globe, which preferably consists of two halves. This is a very practical means of achieving the symmetrical arrangement of diaphragms and detectors in a device that is simple and economical to manufacture. It also ensures without additional expense that the reference and specimen areas will be illuminated with diffuse light.

It will be advantageous for the light source to be positioned between two arms in two mounts in such a way that the arms will prevent the specimen and reference areas from being illuminated directly. In other words, the arms will also screen off the light coming directly from the light source, so that additional components, especially diaphragms and similar structures will not be necessary.

In one preferred embodiment, each arm is secured in grooves in the halves of the globe. This is a simple means of mounting and securing the detectors in relation to the diaphragms that is definite and correct for the operating conditions. Manufacture and assembly are also facilitated, because the mounts or arms are easy to introduce into the grooves.

In one preferred embodiment, the globe has two essentially similar halves, between which two intermediate rings are positioned that serve as mounts for the light source, which is preferably a light-emitting diode. The lead wires of the diode are easy to clamp between the rings if one of the rings has a bead that is engaged by a corresponding projection on the other. A globe of this type can be mounted and assembled with little handling in such a way that the light source will lie in a definite position in the plane of symmetry between the two halves of the globe.

Further advantages and characteristics of the invention will be evident from the embodiment that will now be specified with reference to the drawings, in which

DETAILED DESCRIPTION OF THE INVENTION

Figure 1:
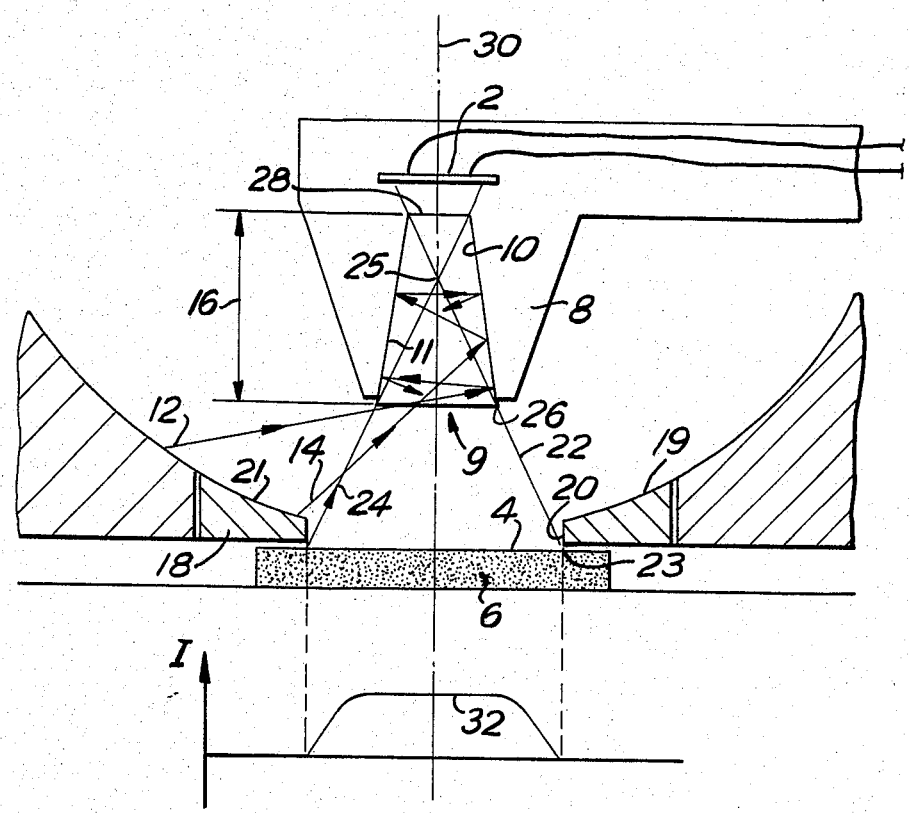
FIG. 1 is a schematic representation of an instrument with a photodetector and associated conical diaphragm according to the invention.

FIG. 1 shows a photodetector 2 that picks up light reflected from a specimen area 4, which is a specific part of the surface of a reaction area 6 in which chemical reactions occur by known processes between the components of a body fluid (like blood or urine) and reagents on a test strip. Color changes that occur as the result of the chemical reactions are quantitatively detected by the detector, which has electronic detection circuitry that will not be specified in greater detail here.

There is a diaphragm 8 between detector 2 and specimen area 4. Characteristic of the design of diaphragm 8 is that it is not adjacent to a particular point of the path of light rays but that the aperture 9 that penetrates it and is limited by diaphragm surface 10 extends over a distance 16 along the path. In the sectional view in FIG. 1, the lines of intersection of diaphragm surface 10 form two straight lines on both sides of the axis 30, which is the axis of symmetry of both the path of light and of the diaphragm system. Geometrically, diaphragm surface 10 is the generating surface of a truncated cone with a preferably but not necessarily circular cross-section. The truncated cone symmetrically surrounds axis 30 along distance 16. Diaphragm 8 has an upper edge 28 facing photodetector 2 and a lower edge 26 facing specimen area 4.

The inside area 11 of diaphragm surface 10 is light-absorbent, preferably mat black. It will be immediately obvious from FIG. 1 that the design of the diaphragm employed in the invention will prevent the marginal light rays 12 and 14 that penetrate into diaphragm aperture 9 from reaching photodetector 2. Even the absorbence of the inside area 11 of diaphragm surface 10 will not in practice prevent it from reflecting some marginal light rays 12 and 14. It is essential to the function of the diaphragm employed in the invention that diaphragm surface 10 be designed to repel such reflected components and direct them back to its inside area 11, which faces axis 30, so that they will die out and be almost completely eliminated.

The embodiment illustrated in FIG. 1 has another diaphragm 18 immediately above specimen area 4 with a diaphragm surface 19 that is concave toward the photodetector. Diaphragm 18 also has a mat-black inside area 21 and an aperture that is surrounded by edge 20. Edge 20 has a radius about 10% of larger than the radius of the area 4.

The upper edge 28 and lower edge 26 of diaphragm surface 10 and the border 23 of specimen area 4 in the embodiment illustrated lie in a sheaf of straight lines 22 and 24. Straight lines 22 and 24 intersect and surround axis 30 of symmetry at a point 25 inside aperture 9. Distance 16, the length of diaphragm 8, is preferably at least as long as the outside diameter of lower edge 26.

The arrangement and association of the diaphragms 8 and 18 in the invention allows especially effective evaluation of the light reflected from specimen area 4. The curve 32 of evaluation of specimen surface 4 is shown at the bottom of FIG. 1. It is evident that the intensity I of the light reaching the photodetector increases gradually from the border to the center of the specimen area. This is an advantage because the borders of test-strip reaction areas are often not very homogeneous and should receive less weight in the evaluation. In the central region the curve of evaluation is horizontal because the light leaving that region penetrates almost unobstructed to the detector and its full intensity can be exploited.

Figure 2:
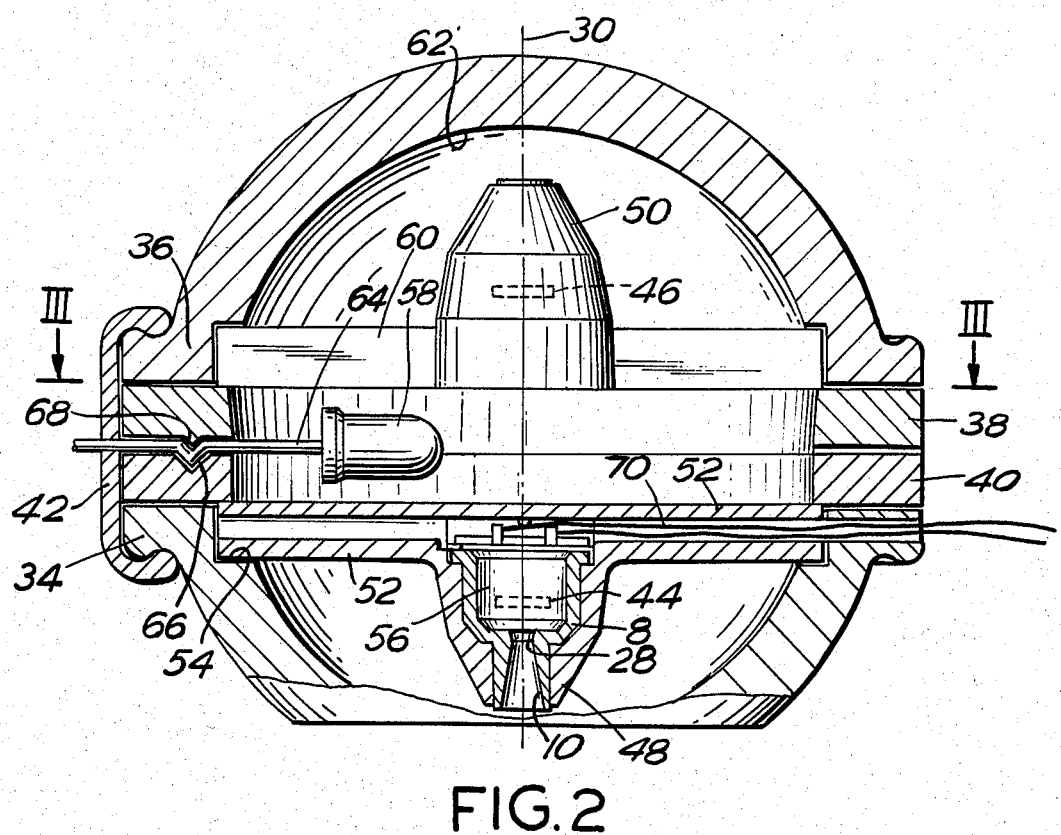
FIG. 2 is a section through an Ulbricht globe with two photodetectors and associated diaphragms according to the invention.

FIG. 2 is a section through an Ulbricht globe that is made up of two halves 34 and 36, between which are positioned two intermediate rings 38 and 40. The resulting globe is held together by tension clamps 42. This globe accommodates in a known way two photodetectors 44 and 46 in mounts 48 and 50 that are identical in design. For the sake of clarity only lower mount 48 will be specified in detail. Mount 48 is secured by arms 52 in a groove 54 in the lower half 34 of the globe. Diaphragm 8, with a conical diaphragm surface 10, is housed coaxially with axis of symmetry 30 inside mount 48.

The embodiment illustrated in FIG. 2 has receptacle-shaped expansions 56 that accept photodetectors 44 and 46. Expansions 56 are preferably in one piece with diaphragm 8, which is made of mat-black plastic, and are shaped to hold photodetectors 44 and 46 securely. Detectors 44 and 46 are positioned in the path of the light beyond upper edge 28 of diaphragm surface 10 in such a way that their light-sensitive surfaces are wider than the light that penetrates the diaphragm. Each light-sensitive surface must in other words be dimensioned and positioned in such a way that none of the light that penetrates diaphragm 8 will get lost.

A light source 58 in the form of a light-emitting diode is positioned between arms 52 and 60 of the upper and lower mounts 48 and 50. Arms 52 and 60 are a simple means of screening light source 58 so that no direct light will strike specimen and reference areas 4 and 62, which are as a result illuminated exclusively with diffuse light. The lead wires of light source 58 are clamped between intermediate rings 38 and 40, with bead 66 and projection 68 simply and reliably securing light source 58. A globe of this type has few components, is easy to mount and assemble, and provides optimal illuminating conditions.

Figure 3:
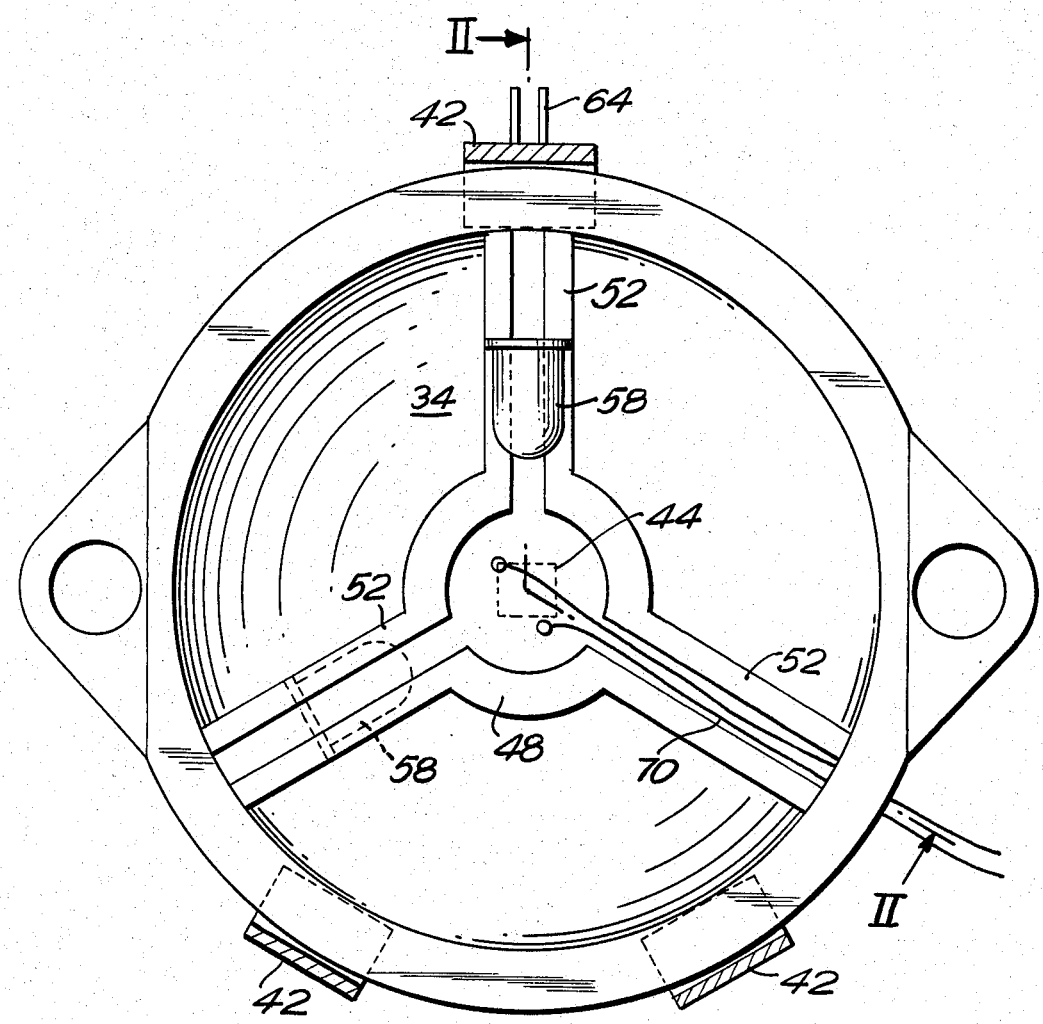
FIG. 3 is a section along the line III—III in FIG. 2.

FIG. 3 is a section along the line III—III in FIG. 2, clearly indicating the position of lower mount 48 in the center of the globe. Three radial arms 2 support mount 48 in half 34 of the globe. Line II—II represents the plane of intersection in FIG. 2. Light source 58 is exactly above one arm 52. It is evident that this arrangement will prevent direct illumination of the specimen area. The lead wires of light source 58 are secured in the manner described above between the intermediate rings, which are not shown in detail here. Current leads 70 extend from photodetector 44 through or inside lead wires 52. Another light source 58, radiating at the same wavelength as the first, is indicated with broken lines, providing a simple means of augmenting the intensity of the light without the necessity of an especially large light source. Preferably, light sources 58, of which there may be more than two, will radiate light of different wavelengths. The individual light sources can be turned on and off to scan a wide range of different types of test strips with one and the same device.

It will be appreciated that the instant specification and claims are set forth by way of illustration and not limitation, and that various modifications and changes may be made without departing from the spirit and scope of the present invention.

What is claimed is:

1. In a reflected-light photometric device for determining the reflectivity of a specimen area which is part of an objective area specifically dedicated for the determination of certain properties of body fluids, having a light source for illuminating the specimen area, and a first photodetector for picking up light reflected from the specimen area, the improvement comprising an opaque first diaphragm with a diaphragm surface shaped essentially as a hollow truncated cone and having a light-absorbing inner area facing the axis of symmetry of the path of light between the specimen area and the detector, means mounting the first diaphragm in said path to essentially symmetrically surround the axis of symmetry along part of its length and taper upwardly toward the detector with the cross-section of its upper edge smaller than that of its lower edge and a second diaphragm disposed closer to the specimen area than the first diaphragm with a light absorbing diaphragm surface facing the photodetector, an aperture that surrounds the specimen area and which is essentially symmetrical to the axis of symmetry of the path of light.

2. The device according to claim 1, wherein the upper and lower edge of the diaphragm surface of the first diaphragm and the border of the specimen area lie approximately in a sheaf of straight lines that intersect and symmetrically surround the axis of symmetry inside the diaphragm.

3. The device according to claim 1, wherein the diaphragms are black at least on their inside surfaces which are in the path of light.

4. The device according to claim 1, wherein the first diaphragm has apertures at both ends thereof.

5. In a reflected-light photometric device for determining the reflectivity of a specimen area which is part of an objective area specifically dedicated for the determination of certain properties having a light source for illuminating the specimen area, and a first photodetector for picking up light reflected from the specimen area, the improvement comprising an opaque first diaphragm with a diaphragm surface shaped essentially as a hollow truncated cone and having a light-absorbing inner area facing the axis of symmetry of the path of light between the specimen area and the detector, means mounting the first diaphragm in said path to essentially symmetrically surround the axis of symmetry along part of its length and taper upwardly toward the detector with the cross-section of its upper edge smaller than that of its lower edge and wherein the light source comprises an Ulbricht globe that diffusely illuminates the specimen area and having an area of the inside surface thereof that serves as the reference area, a second photodetector for detecting the reference property of the reference area and wherein both photodetectors have exactly similar diaphragms.

6. The device according to claim 5, wherein the globe comprises two halves and further comprising means mounting each diaphragm and detector in the globe including radially extending arms.

7. The device according to claim 6, wherein the light source comprises a light emitting element positioned between two of the arms to prevent direct illumination of the specimen and reference areas.

8. The device according to claim 6 or 7, wherein the mounting means comprises a groove on the edge of each half of the globe and receptive of the arms.

9. The device according to claim 6, further comprising two intermediate rings between the halves of the globe and wherein the light source comprises a light-emitting diode having lead wires clamped between the rings, with one ring having a bead that is engaged by a corresponding projection on the other to secure the diode.

10. The device according to claim 6, wherein each diaphragm with the diaphragm surface in the shape of a truncated cone and the mounting means for the photodetectors comprise one component including an expansion connected to the upper edge of the diaphragm surface and configured to receive a photodetector.

11. In a reflected-light photometric device for determining the reflectivity of a specimen area which is part of an objective area specifically dedicated for the determination of certain properties of body fluids, having a light source and an associated Ulbricht's globe for diffusely illuminating the specimen area and having a reference area on the inside surface thereof, a first photodetector for picking up light reflected from the specimen area, a second photodetector for detecting the reference property of the reference area on the inside surface of the Ulbricht's globe, the improvement wherein the light source comprises a light emitting diode, and further comprising means mounting both photodetectors in the Ulbricht's globe, comprising radially extending arms and directing the first photodetector towards the specimen area and the second photodetector towards the inner surface of the Ulbricht's globe and a diaphragm positioned between the first photodetector and the specimen area and configured such that essentially only light from the specimen area passes to the first photodetector.

12. The device according to claim 11, wherein the globe comprises two halves and wherein the radially extending arms are supported between the two halves.

13. The device according to claim 12, wherein the light emitting element is positioned between two of the arms to prevent direct illumination of the specimen and reference areas.

14. The device according to claim 12 or 13, wherein the mounting means further comprises a groove on the edge of each half of the globe and receptive of the arms.

15. The device according to claim 12, further comprising two intermediate rings between the halves of the globe and wherein the light-emitting diode has lead wires clamped between the rings, with one ring having a bead that is engaged by a corresponding projection on the other to secure the diode.

16. The device according to claim 11, wherein the diaphragm mounting means for the first photodetector comprises one component including an expansion connected to an upper edge of the diaphragm surface and configured to receive the first photodetector.

* * * * *